(12) United States Patent
Shukla et al.

(10) Patent No.: US 8,409,634 B2
(45) Date of Patent: Apr. 2, 2013

(54) ANTI-OXIDANT HERBAL COMPOSITION

(76) Inventors: Mukesh Harilal Shukla, Surendranagar (IN); Mitesh Pradipkumar Trivedi, Gandhinagar (IN)

( * ) Notice: Subject to any disclaimer, the term of this patent is extended or adjusted under 35 U.S.C. 154(b) by 0 days.

(21) Appl. No.: 13/291,625

(22) Filed: Nov. 8, 2011

(65) Prior Publication Data

US 2013/0040002 A1    Feb. 14, 2013

(30) Foreign Application Priority Data

Aug. 9, 2011   (IN) .......................... 2240/MUM/2011

(51) Int. Cl.
*A01N 65/00* (2009.01)
(52) U.S. Cl. ...................................................... 424/725
(58) Field of Classification Search ........................ None
See application file for complete search history.

(56) References Cited

U.S. PATENT DOCUMENTS 7,514,105 B2 *   4/2009   Qazi et al. ..................... 424/725

* cited by examiner

*Primary Examiner* — Michael Meller
(74) *Attorney, Agent, or Firm* — Rajesh Vallabh; Foley Hoag LLP

(57) ABSTRACT

The present disclosure relates to a novel Anti-Oxidant Herbal composition comprising *Termanalia arjuna* extract, *Camellia sinensis* extract, and Trikatu extract in specific weight percentages and optionally at least one carrier. The present disclosure further relates to use of the composition for treatment and/or prevention of hyperlipidemia and/or Ischemic heart disease. The present disclosure also relates to a method of preparation of the composition.

1 Claim, No Drawings

ANTI-OXIDANT HERBAL COMPOSITION

FIELD OF INVENTION

The present disclosure relates to a novel Anti-Oxidant Herbal composition comprising *Termanalia arjuna* extract, *Camellia sinensis* extract, and Trikatu extract in specific weight percentages and optionally at least one carrier. The present invention further relates to use of the composition for treatment and/or prevention of hyperlipidemia and/or Ischemic heart disease. The present disclosure also relates to a method of preparation of the composition.

BACKGROUND OF THE INVENTION

Heart is a vital, fist-sized organ which is located in the left side of chest cavity, responsible for pumping blood throughout blood vessels by repeated, rhythmic contractions. Diseases affecting the heart may be structural or functional. Anything which damages heart or decreases heart's supply of oxygen, makes it less efficient, reduces its ability to fill and pump, disrupts a coordinated relationship between the heart, kidneys, and blood vessels and harms not only the heart but the rest of the body as well.

Heart disease, or cardiovascular disease, accounts for 30 percent of deaths worldwide, according to the World Health Organization (WHO). In the United States, almost 700,000 people die from heart disease each year. In India in the past five decades, rates of coronary disease among urban populations have risen from 4 percent to 11 percent. Nearly 50 percent of cardiovascular diseases-related deaths in India occur below the age of 70, compared with just 22 percent in the West. This trend is particularly alarming because of its potential impact on one of Asia's fastest-growing economies. In 2000, for example, India lost more than five times as many years of economically productive life to cardiovascular disease than did the U.S., where most of those killed by heart disease are above retirement age.

Nearly 95 percent of people who develop fatal cardiovascular disease have at least one of the following major risk factors: high blood cholesterol, high blood pressure, diabetes, besides a poor diet and overweight. In addition, cardiovascular diseases can also occur in absence of traditional risk factors.

Among the leading new potential culprits, LDL-C (low density lipoprotein cholesterol) puts us in the high risk zone as far as heart diseases are concerned. The cholesterol gets deposited in the arteries making them narrower and narrower. As a result the blood supply to the heart gets thwarted. This leads to heart attacks.

Several conventional drug therapies are commonly used in addition to the practice of healthy lifestyle. Prescription drug choices to treat elevated LDL-C are the bile acid sequestrants (cholestyramine and colestipol), nicotinic acid (niacin), gemfibrozil, probucol, and clofibrate. Niacin, in particular, has troublesome side effects (e.g. itching, flushing). Other types of prescription drugs such as HMG-CoA reductase inhibitors, commonly known as statins drugs, are commonly used nowadays. Examples are: Lipitor/atorvastatin, Baycol/cerivastatin, Lescol/fluvastatin, Mevacor/lovastatin, Pravachol/pravastatin, Crestor/rosuvastatin, and Zocor/simvastatin. However, these drugs have demonstrated side effects such as muscle pain, muscle weakness, fatigue, peripheral neuropathy, memory/thinking problems, and mood/personality changes, cognitive problems among other symptoms. Simvastatin could be a cause of disrupted sleep in some patients. Lovastatin also has side effects particularly including liver dysfunction.

Alternatives to prescription drugs are being viewed with increasing interest especially since the withdrawal from the market of the prescription cholesterol-lowering drug Baycol after numerous deaths associated with its use.

Ischaemic heart disease (IHD), characterized by reduced blood supply to the organs, is a condition of recurring chest pain or discomfort that occurs when a part of the heart does not receive enough blood. The signs and symptoms of ischemic heart disease may develop slowly as arteries gradually become blocked, or they may occur quickly if an artery suddenly becomes blocked. Some people with ischemic heart disease have no symptoms at all, while others may have severe chest pain (angina) and shortness of breath that can pose a risk of heart attack.

Several conventional drug therapies are commonly used for treatment of Ischemic heart disease. Severe symptoms that are not relieved by medication alone are treated with surgical procedures in addition with following healthy lifestyle.

Conventional drugs falling in various groups viz. Angiotensin Converting Enzyme Inhibitors, for example, Accuprila (quinapril), Altacea (ramipril), Capotena (captopril); Alpha & Beta Blockers, for example, Carduraa (doxazosin mesylate), Hytrina, Inderala (propanolol), Lopressora; Calcium Channel Blockerse, for example, Verapamil (Calana, Isoptina) and diltiazem; Cholesterol Lowering Drugs; Diuretics; Digitalis; Nitrates; Anticoagulants are used for treating IHD.

However, there exist a number of side effects for the existing therapies. Such side effects can include skin rash, dry hacking cough, dizziness, sleepiness, nasal congestion and fatigue or tiredness, edema. Many of the Cholesterol Lowering Drugs cause a variety of gastrointestinal symptoms such as constipation, diarrhea, bloating, excess gas, and abdominal distress. Many of these agents may also alter the function of the liver and the liver enzymes. Diuretics include excess loss of fluid leading to dehydration, excess loss of potassium, which may be life threatening. Digitalis may include visual difficulties as well as cardiac arrhythmias. The later may, at times, be life threatening.

The existing medications cause a number of side effects as discussed above. Therefore, alternatives to prescription drugs are being viewed with increasing interest in the treatment of Ischemic heart diseases and high cholesterol.

The herbal kingdom offers a few remedies for effective treatment of Ischemic Heart Diseases and high cholesterol. Further, the increasing hectic and stressful lifestyles of the people especially due to overworking, stress, fatigue, among other causes, demands new and more effective herbal compositions for appreciable relief up to the satisfaction of the patients.

Accordingly, there still exists an ongoing need for developing a new herbal composition which is safe and effective against Ischemic Heart Diseases and high cholesterol yet devoid of side effects and toxicity so as also to rejuvenate the general health. The present disclosure satisfies these needs.

OBJECTS OF THE INVENTION

An object of the invention is to provide a novel Anti-Oxidant Herbal composition comprising an extract of *Termanalia arjuna*, an extract of *Camellia sinensis*, and an extract of Trikatu in specific weight percentages, and optionally at least one carrier.

A further object of the present invention is to use the composition for treatment and/or prevention of hyperlipidemia, by administrating a therapeutically effective amount of the composition to a subject in need thereof.

Yet a further object of the present invention is to use this composition for treatment and/or prevention of Ischemic heart disease, by administrating a therapeutically effective amount of the composition to a subject in need thereof.

A further object of the present invention is to provide a method of preparation of the herbal composition.

SUMMARY OF THE INVENTION

The present invention relates to a novel Anti-Oxidant Herbal composition comprising an extract of *Termanalia arjuna*, an extract of *Camellia sinensis*, and an extract of Trikatu in specific weight percentages.

In one embodiment, the herbal composition of the present invention comprises 30-50% by weight of *Termanalia arjuna* extract, 30-50% percent by weight of *Camellia sinensis* extract, and 10-30% by weight of Trikatu.

The herbal composition of the present disclosure can optionally contain at least one carrier.

The present disclosure further relates to use of the composition of the present invention for treatment and/or prevention of hyperlipidemia, by administrating a therapeutically effective amount of the composition to a subject in need thereof.

The present invention further relates to use of the composition of the present invention for treatment and/or prevention of Ischemic heart disease, by administrating a therapeutically effective amount of the composition to a subject in need thereof.

The present invention further relates to a method of preparation of the composition.

DETAILED DESCRIPTION OF THE INVENTION

The present disclosure is directed to a novel Anti-Oxidant Herbal composition comprising *Termanalia arjuna* extract, *Camellia sinensis* extract, and Trikatu extract, and optionally at least one carrier, for use in treatment and/or prevention of Ischemic Heart Disease and/or Hyperlipidemia.

The term "Hyperlipidemia" as used herein, refers to a condition of elevated blood lipids/fats including cholesterol, cholesterol esters, phospholipids, triglycerides or lipoproteins in the bloodstream. Elevated low density lipoprotein-cholesterol (LDL-C) and reduced high density lipoprotein-cholesterol (HDL-C) levels are well recognized coronary heart disease (CHD) risk factors. When low density lipoproteins (LDL) are oxidized, they promote inflammation and lead to plaque formation or atherosclerosis.

The term "ischemic heart disease" or "ischaemic heart disease" or IHD, as used herein, refers to a disease characterized by reduced blood supply of the heart muscle, usually due to atherosclerosis. Its risk increases with age, smoking, hyperlipidemia (high cholesterol and high fats in the blood), diabetes, and hypertension (high blood pressure), and is more common in men and those who have close relatives with ischemic heart disease. The main causes of atherosclerosis (the disease process underlying IHD) include hyperlipidaemia, hypertension (high blood pressure), diabetes, and age, male sex, anxiety, stress, smoking, and family history. Atherosclerosis can lead to coronary heart disease, stroke, claudication and associated morbidity and mortality.

Elevated cholesterol levels lead to the formation of fatty streaks and calcified plaques, and abnormalities in vascular functioning in both animals and humans. Population studies have shown that lipid-lowering strategies can reduce the risk of developing atherosclerotic disease, particularly myocardial infarction.

The term "subject" used herein refers to mammals, most preferably humans.

*Terminalia arjuna*:

*Terminalia arjuna* is a deciduous medicinal tree of genus *Terminalia*, and is abundantly found in India. *Terminalia arjuna* tree bark powder has been shown to have an antioxidant and cholesterol lowering effect. *Terminalia arjuna* has also been shown to act as a therapeutic and preventive modulator in experimentally induced myocardial infarction.

Botanical Classification:
Family: Combretaceae
Genus: *Terminalia*
Species: *T. arjuna*

*Camellia sinensis*:

*Camellia sinensis* is native to mainland China, South and Southeast Asia. Common names include tea plant, tea tree, and tea shrub.

Botanical Classification:
Family: Theaceae
Genus: *Camellia*
Species: *C. sinensis*

Dried leaves from the *Camellia sinensis* plant are processed into three types of tea: oolong tea, black tea, and green tea. In making green tea, the tea leaves are stabilized by moist or dry heat which destroys the enzyme polyphenoloxidase and thus, prevents oxidation of polyphenols. These polyphenols are the main biologically active ingredients in green tea. Catechins, a chemical group of polyphenols possessing antioxidant properties (protects cells from free radical-mediated damage), comprises of epigallocatechin-3 gallate (ECGC), epigallocatechin, and epicatechin-3-gallate. Polyphenol extracts prepared from *Camellia sinensis* exhibit antimutagenic, anticarcinogenic, antioxidant and antipromotional effects.

Trikatu:

Trikatu is a herbal combination containing equal parts of:
fruits of *Piper Nigrum*;
fruits of *Piper longum* and
Rhizomes of *Zingiber officinalis*;

This combination streamlines metabolism of the body, which is the reason why the combination has been indicated in a wide range of health problems. This herbal combination of three ingredients is safe, digestive, carminative, anti-flatulent and effective in dyspepsia, and further improves gastric function. Trikatu possess Anti-oxidative property and radical scavenging activity.

Herbal ingredients and amounts used in the herbal composition of the present invention are set forth in Table 1. It should be understood that the proportions of the individual herbs may vary. In particular, proportions of one or more of the components may vary in order to optimize the treatment effects to suit individual patients.

TABLE 1

Preferred Composition of herbal ingredients and their biomarkers:

| S. No. | Botanical Name | Standardised Common Name | Part Used | Bio-markers | Percent by weight (%) of the composition |
|---|---|---|---|---|---|
| 1 | *Terminalia arjuna* | Arjuna | Bark | About 40% arjunitine | 30-50% |

TABLE 1-continued

Preferred Composition of herbal ingredients and their biomarkers:

| S. No. | Botanical Name | Standardised Common Name | Part Used | Bio-markers | Percent by weight (%) of the composition |
|---|---|---|---|---|---|
| 2 | *Camellia sinensis* | Tea | Leaves | About 35% polyphenols | 30-50% |
| 3 | *Piper Nigrum*, *Piper longum* and *Zingiber officinalis* | Trikatu | 1. Fruits of *Piper nigrum*; 2. Fruits of *Piper longum*; and 3. Rhizomes of *Zingiber officinalis*; in equal proportions | About 25% of mixture of piperine and Gingerol | 10-30% 20-30% |

*Termanalia arjuna*, *Camellia sinensis* and Trikatu have been used individually for health promoting and varied therapeutic purposes. However, the herbal composition of the present disclosure is a unique combination that has been developed to provide therapeutic benefits in the treatment and/or prevention of Ischemic heart disease and/or hyperlipidemia.

An important aspect of the herbal composition of the present invention is that the composition comprises of a mixture of herbal extracts, which provide more benefit than a single herb. An unexpected synergistic effect is exhibited by the combination of various ingredients in the present herbal composition. Strategic combination of herbal ingredients of the present invention exhibits beneficial pharmacological effects when optimally combined. Active ingredients of the herbs are preferably combined in such a manner as to optimize and enhance the pharmacological effects with minimal or no adverse toxic reactions (which become a distinct possibility if the herbs are used singly at a concentration of 100%). An additional advantage of this herbal composition is that it minimizes the risk of developing drug resistance.

The herbal composition described herein can be used as an alternative to conventional drugs or treatments and has been found to effectively treat or maintain a wide range of physiological and pathological conditions in the human body, especially in individuals with hyperlipidemia.

An embodiment of the present disclosure provides use of the herbal composition of the present invention for the treatment and/or prevention of hyperlipidemia, by administrating a therapeutically effective amount of the composition to a subject in need thereof.

A further embodiment of the present disclosure provides use of the herbal composition of the present invention for the treatment and/or prevention of Ischemic Heart Disease, by administrating a therapeutically effective amount of the composition to a subject in need thereof.

In yet another embodiment, the beneficial uses of the herbal composition of the present disclosure include, but not limited to:
(a) anti-hyperlipidemic (The composition reduces high cholesterol/lipids, the building block for plaques);
(b) anti-atherosclerotic (The composition prevents plaque formation);
(c) antioxidant (The composition reduces lipid peroxidation, and is helpful because plaques are formed by oxidized LDL and other lipids);
(d) anti-stress (The composition reduces anxiety and stress, known causes of plaque build-up);
(e) cardiotonic (The composition enables optimal heart function by acting on the cardiac smooth muscle); and
(g) Cardioprotective (The composition protects the heart from damage causing toxins).

Active compounds responsible for specific therapeutic activity can be found in higher concentrations in specific parts of medicinal plants and in lower concentrations in other specific parts. Specific part of a medicinal plant having higher concentration is selected and processed for preparing the extracts as used in the preparation of the composition of the present invention. Preferably, extracts of *Termanalia arjuna* and *Camellia sinensis* are obtained from barks and leaves of respective plants. Trikatu as used in the preparation of the present invention is prepared or obtained from extracts of fruits of *Piper longum*, fruits of *piper nigrum* and rhizomes of *Zingiber officinalis* in equal parts.

Extracts of different parts of above mentioned herbal plants can be used in form of a dried powder, which facilitates preparation of herbal composition of the present disclosure.

The plant extracts composition of the present disclosure can be administered orally.

Dosage form of the herbal composition can be selected from a group comprising of tablet, capsule, powder, beads, pellets, granules, solution, syrup, suspension, oleoresin, and emulsion. A preferred dosage form is one of a tablet, capsule, powder, syrup, or granule. More preferably, the dosage form is one of a capsule, tablet, or syrup.

The herbal composition of the present disclosure can be prepared by using any common technique available in the art.

The herbal composition of the present disclosure comprises 30-50% by weight of *Termanalia arjuna* extract, 30-50% percent by weight of *Camellia sinensis* extract and 10-30% by weight of Trikatu.

The herbal composition of the present disclosure optionally contains at least one carrier. The carrier as used herein is selected from a group comprising of diluent, binder, disintegrant, glidant, and lubricant. There may be one or more carriers used in the preparation of composition.

Diluents are inert excipients that are used to adjust the bulk in a pharmaceutical composition. Commonly used diluents comprise of lactose, dicalcium phosphate, micro crystalline cellulose, kaolin, mannitol and starch. In an embodiment, Diluents can be used in a range of 2 to 5% by weight of the composition.

Binders are utilized in a pharmaceutical composition to impart cohesive force to the composition powder, which allows the powder materials to retain their integrity once they are compressed. Commonly used binders comprise of carboxymethyl cellulose, methyl cellulose, polyvinylpyrrolidone, ethyl cellulose, pregelatinized starch, and gelatin. In an embodiment, binders can be used in a range of 1 to 5% by weight of the composition.

Disintegrant is an excipient or a mixture of excipients added to facilitate breakup of binded powdered materials forming the composition. Dried and powdered corn starch or potato starch are widely used disintegrants. These disintegrants have a good affinity towards water and swell when moistened, and result in rupturing the tablet. A group of materials known as super-disintegrants comprising croscarmelose, cross-linked cellulose, crosprovidone, cross-linked polymer, sodium starch glycolate, and cross-linked starch can be used in the composition. In an embodiment, disintegrants can be used in a range of 2 to 5% by weight of the composition.

Lubricants are used in a pharmaceutical composition to prevent adhesion of a tablet material to the surface of dyes and punches. Commonly used lubricants comprise of magnesium stearate, calcium stearate, talc, stearic acid, hydrogenated vegetable oils, and PEG. In an embodiment, the lubricants can be used in a range of 0.5 to 4% by weight of the composition.

Glidants are used in a pharmaceutical composition to improve flow characteristics of powder materials. Colloidal silicon dioxide and anhydrous silica are commonly used glidants. Talc may serve as a combined lubricant/glidant. Glidants can be used in a range of 0.5 to 5% by weight of the composition.

Extracts procured from different plant parts are also tested for standard laboratory analytical tests as TLC, Identification, MS., Assay by Spectrophotometer, Heavy Metals, and Microbial Profile.

Herbal composition of the present disclosure can be prepared by techniques commonly available in the art.

An exemplary and generalized process for preparing the plant extracts/herbal composition of the present disclosure is described below in a stepwise manner.

a) Sifting extracts of *Termanalia arjuna, Camellia sinensis*, and Trikatu (*Piper longum, piper nigrum* and *Zingiber officinalis* in equal parts) through 20# and optionally sifting at least one carrier through 40# and;

b) Mixing the sifted extracts of step a) and optionally;

c) Granulating the mixed sifted extracts of step b) using a solvent and optionally;

d) Drying granules formed from step c) and optionally;

e) Sifting dried granules of step d) through 20# and optionally;

f) Mixing materials of step b) or e) with the carrier from step a); and g) Filling of material of step f) into capsules or compressing into tablets.

To obtain a homogenized composition, material obtained from step (f) is shifted to the homogenizer for further process.

Processing steps such as sifting, granulation, drying, mixing, filling of capsule, soft gelatine capsule, syrup, tablet compression, as described above, can be performed according to well known techniques available in the art.

EXAMPLES

The present invention is further explained in the form of following examples. However it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1

Herbal Composition of the Present Invention in Capsule Form in Table 2

TABLE 2

| Ingredients | Mg |
|---|---|
| Extract of *Termanalia arjuna* | 200 |
| Extract of *Camellia sinensis* | 200 |
| Extract of Trikatu | 100 |
| Total | 500 |

Example 2

Standard Laboratory Analytical Tests for *Terminalia arjuna* Dry Extract in Table 3

TABLE 3

*Terminalia arjuna* Dry extract

| | Specified Test | Result | Specification |
|---|---|---|---|
| 1) Physiochemical | | | |
| a. | Description | Reddish brown coloured dry powder with astringent taste | Reddish brown coloured dry powder with astringent taste |
| b. | Solubility in ASE 50 | 72.59% | NLT 50% |
| c. | pH of 1% w/v soln. | 4.62 | 3-7 |
| d. | Ash content | 7.96% | NMT 10% |
| e. | Loss on drying | 4.85% | NMT 7% |
| f. | Heavy metals | Complies | NMT 20 ppm |
| 2) Active Ingredients | | | |
| Tannins | | 26.63% | NLT 20% (On dry basis) |
| 3) Micro Biologicals | | | |
| Total plate count | | 720 Cfu/gm | NMT 1000 Cfu/gm |
| Total yeast mould | | 50 Cfu/gm | NMT 100 Cfu/gm |
| E. coli | | ABSENT | ABSENT |
| Salmonella spp. | | ABSENT | ABSENT |
| S. aereus | | ABSENT | ABSENT |

Example 3

Standard Laboratory Analytical Tests for *Camellia sinensis* Dry Extract in Table 4

TABLE 4

*Camellia sinensis* dry extract

| | Specified Test | Result | Specification |
|---|---|---|---|
| 1) Physiochemical | | | |
| a. | Description | Brown coloured dry powder | Brown coloured dry powder |
| b. | Solubility in Water | 72.11% | NLT 50% |
| c. | Loss on drying | 4.41% | NMT 7% |
| d. | pH of 1% w/v soln. | 4.43 | 3-7 |
| e. | Ash content | 6.10% | NMT 15% |
| f. | Heavy metals | Complies | NMT 10 ppm |

TABLE 4-continued

*Camellia sinensis* dry extract

| Specified Test | Result | Specification |
|---|---|---|
| 2) Active Ingredients | | |
| Polyphenols | 51.40% | NLT 50% (On dry basis) |
| 3) Micro Biologicals | | |
| Total plate count | 790 Cfu/gm | NMT 1000 Cfu/gm |
| Total yeast mould | 40 Cfu/gm | NMT 100 Cfu/gm |
| *E. coli* | ABSENT | ABSENT |
| *Salmonella* spp. | ABSENT | ABSENT |
| *S. aereus* | ABSENT | ABSENT |

Example 4

Standard Laboratory Analytical Tests for Trikatu Dry Extract in Table 5

TABLE 5

Trikatu dry extract

| | Specified Test | Result | Specification |
|---|---|---|---|
| 1) Physiochemical | | | |
| a. | Description | Light Green coloured dry powder with characteristic aromatic odour and pungent taste | Light Green coloured dry powder with characteristic aromatic odour and pungent taste |
| b. | Solubility in Alcohol 90% v/v | 21.56% | NLT 20% |
| c. | Loss on drying | 4.11% | NMT 7% |
| d. | pH (1% w/v soln.) | 6.40 | Between 4-7 |
| e. | Heavy metals | Complies | NMT 20 ppm |
| f. | Ash content | 2.21% | NMT 15% |
| 2) Active Ingredients | | | |
| | Volatile Oil | 4.10% | NLT 3% |
| 3) Micro Biologicals | | | |
| | Total plate count | 720 Cfu/gm | NMT 1000 Cfu/gm |
| | Total yeast mould | 30 Cfu/gm | NMT 100 Cfu/gm |
| | *E. coli* | ABSENT | ABSENT |
| | *Salmonella* spp. | ABSENT | ABSENT |
| | *S. aereus* | ABSENT | ABSENT |

Example 5

Clinical Investigation of the Composition of the Present Invention

The pilot study to check the effectiveness of the composition in patients has been conducted. The voluntary Clinical Trials of the patients have been observed and undertaken (Table 6). The composition in dosage form of 500 mg hard gelatin capsule has been administered in dosing schedule of 2 capsules 2 times a day for duration of three months. The clinical observation for three months suggests further duration of course to acquire more prolific results. The drug is safe and has significant efficacy even in case of diabetes mellitus. The composition fetched results with safety and efficacy and further without any interaction even if taken with the conventional drug. The composition has pathophysiological significance with safety and efficacy.

TABLE 6

CLINICAL TRIAL OBSERVATION

| S. No. | Patient | Report Date before and after administration of the composition of the present invention | S. Cholesterol | HDL | CH/HD | S. Triglyceride | V.L.D.L. | LDL | LD/HD (Ratio) |
|---|---|---|---|---|---|---|---|---|---|
| 1. | VN F/45 | Before- Mar. 1, 2011 After- Jun. 2, 2011 | 256.2 216.3 | 66.2 80 | 3.9 207 | 217.4 201.7 | 12.9 8.98 | 130.5 146.2 | 1.97 1.82 |
| 2. | VS M/52 | Before- Mar. 2, 2011 After- Jun. 1, 2011 | 226.9 178 | 63.2 48.7 | 3.6 3.7 | 227.6 201.7 | 30.1 40.37 | 156 165.76 | 2.47 3.4 |
| 3. | IS F/40 | Before- Mar. 3, 2011 After- Jun. 2, 2011 | 226.2 226.2 | 64.5 64.5 | 3.5 3.5 | 149 149 | 30.2 30.2 | 160.2 160.2 | 2.48 2.48 |
| 4. | JB F/48 | Before- Mar. 4, 2011 After-Jun. 4, 2011 | 236.3 167.4 | 40.56 80.4 | 5.8 2.1 | 156.2 137.5 | 30 28.6 | 151.2 137.2 | 3.7 1.71 |
| 5. | RJ F/45 | Before- Mar. 5, 2011 After- Jun. 4, 2011 | 249.1 229.6 | 88.2 70.6 | 2.83 3.3 | 121 156 | 23 25.2 | 136 151 | 1.54 2.14 |
| 6. | BP F/39 | Before- Mar. 5, 2011 After-Jun. 6, 2011 | 268 216.3 | 74 81.2 | 3.6 2.7 | 150 117.3 | 29 24.2 | 151 132 | 2.04 1.63 |
| 7. | PP M/38 | Before- Mar. 6, 2011 After-Jun. 8, 2011 | 248 206 | 56 56 | 4.43 3.68 | 170 164 | 32.8 32.8 | 120 117.2 | 2.14 2.09 |
| 8. | PD M/33 | Before- Mar. 6, 2011 After-Jun. 7, 2011 | 236.3 174.8 | 41.2 47.6 | 5.7 3.67 | 81.6 80.3 | 13.4 16.06 | 155.4 111.2 | 3.76 2.33 |
| 9. | HP M/32 | Before- Mar. 6, 2011 After- Jun. 10, 2011 | 223.2 155.5 | 79 89 | 2.8 1.8 | 199.6 192.6 | 26.1 24 | 153.2 136.8 | 1.94 1.54 |
| 10. | RG M/40 | Before- Jun. 7, 2011 After-Jun. 9, 2011 | 241 182 | 82 49 | 2.94 3.71 | 110 120 | 22 24 | 109 109 | 1.33 2.22 |
| 11. | DR M/43 | Before- Mar. 8, 2011 After- Jun. 13, 2011 | 530.1 517.8 | 46 56.1 | 11.5 9.2 | 168.4 139.7 | 39 27 | 210.2 167.2 | 4.57 2.99 |
| 12. | NP F/80 | Before- Mar. 8, 2011 After-Jun. 7, 2011 | 228 164.6 | 61 67 | 3.73 2.5 | 182 179.5 | 28.1 27 | 156 137 | 2.56 2.04 |
| 13. | DM F/43 | Before- Mar. 8, 2011 After- Jun. 10, 2011 | 530.1 517.8 | 46 56 | 11.5 9.2 | 198.4 190.7 | 29 27 | 210.2 167.2 | 4.57 2.99 |
| 14. | BJ F/42 | Before- Mar. 9, 2011 After- Jun. 11, 2011 | 221.8 166.3 | 89 94 | 2.5 1.8 | 151.3 143.2 | 17 25.8 | 129 110 | 1.45 1.17 |

TABLE 6-continued

CLINICAL TRIAL OBSERVATION

| S. No. | Patient | Report Date before and after administration of the composition of the present invention | S. Cholesterol | HDL | CH/HD | S. Triglyceride | V.L.D.L. | LDL | LD/HD (Ratio) |
|---|---|---|---|---|---|---|---|---|---|
| 15. | BA F/30 | Before- Mar. 10, 2011 After- Jun. 14, 2011 | 238 223.1 | 91.2 94 | 2.6 2.4 | 176 173 | 32 30 | 151.4 138.6 | 1.66 1.47 |
| 16. | BR M/47 | Before- Mar. 12, 2011 After- Jun. 11, 2011 | 231.6 193.1 | 67.8 86.1 | 3.4 2.2 | 148.3 144.4 | 28 23.4 | 152 149 | 2.24 1.73 |
| 17. | AV F/45 | Before- Mar. 14, 2011 After- Jun. 17, 2011 | 258 237 | 89 54 | 2.4 4.39 | 197 179 | 35.8 35.8 | 147.2 147.2 | 1.65 2.73 |
| 18. | GZ M/56 | Before- Mar. 19, 2011 After- Jun. 18, 2011 | 192 180 | 56 46 | 3.43 3.91 | 204 164 | 40.8 40.8 | 95.2 95.2 | 1.7 2.06 |
| 19. | KP M/46 | Before- Mar. 21, 2011 After- Jun. 20, 2011 | 220 180 | 55 53 | 3.04 3.4 | 235 185 | 37 37 | 92 90 | 1.07 1.7 |
| 20. | PA M/46 | Before- Mar. 30, 2011 After- Jun. 30, 2011 | 231.5 222 | 53.2 51.8 | 4.35 4.2 | 219.9 198 | 41.76 40.76 | 71.74 68.74 | 1.35 1.33 |
| 21. | BSP M/45 | Before- Mar. 28, 2011 After- Jun. 30, 2011 | 246.5 227.8 | 42.02 43.06 | 5.86 5.03 | 93.5 92 | 18.7 17.3 | 185.7 167.02 | 3.7 3.88 |
| 22. | HS M/47 | Before- Apr. 22, 2011 After- Jul. 22, 2011 | 239.5 212.2 | 43.6 50.6 | 5.5 4.2 | 156.2 139.5 | 30.8 36.5 | 158.9 120.9 | 3.6 2.4 |
| 23. | RR M/58 | Before- Apr. 22, 2011 After- Jul. 21, 2011 | 227 140.7 | 44.06 45.04 | 5.1 3.12 | 141.8 129.2 | 19.04 18 | 130 126 | 2.95 2.8 |
| 24. | SS F/50 | Before- Apr. 21, 2011 After- Jul. 26, 2011 | 258.56 217.6 | 40.3 50.8 | 6.4 4.3 | 161.5 141.4 | 29.1 28.3 | 152 138.5 | 3.77 2.73 |
| 25. | SGS F/50 | Before- Apr. 24, 2011 After- Jul. 26, 2011 | 246.1 217.6 | 44.05 50.08 | 5.6 4.3 | 147.4 141.4 | 28.2 28.3 | 141.2 138.5 | 3.2 2.77 |
| 26. | RV F/40 | Before- Apr. 25, 2011 After- Jul. 30, 2011 | 248 223 | 71 78 | 3.5 2.9 | 169.7 166 | 33.1 30.2 | 155.3 149 | 2.19 1.91 |
| 27. | DV M/39 | Before- Apr. 26, 2011 After- Jul. 27, 2011 | 223 169.9 | 41.4 48.7 | 5.4 3.5 | 197.3 187.1 | 30.2 37.42 | 156 83.78 | 3.8 1.72 |
| 28. | GS M/57 | Before- Apr. 27, 2011 After- Jul. 26, 2011 | 234.4 226.23 | 45.06 48.9 | 5.2 4.6 | 153.8 153 | 26.2 21.2 | 145.2 120.2 | 3.23 2.45 |
| 29. | LP F/65 | Before- Apr. 28, 2011 After- Jul. 30, 2011 | 235.4 196.8 | 62.7 52.2 | 3.8 3.8 | 137 152 | 31 31.06 | 147.2 156.1 | 2.35 2.99 |
| 30. | PL M/46 | Before- Apr. 30, 2011 After- Jul. 30, 2011 | 231.5 222 | 53.2 51.8 | 4.35 4.2 | 211.9 138 | 31.76 21.17 | 71.74 68.74 | 1.35 1.33 |

We claim:

1. A pharmaceutical composition for treating ischemic heart disease consisting essentially of therapeutically effective amounts of *termanalia arjuana* extract, *camellia sinensis* extract, *piper nigrum* extract, *piper longum* extract and *zingiber officinalis* extract.

* * * * *